United States Patent
Osaki et al.

(10) Patent No.: US 8,089,629 B2
(45) Date of Patent: Jan. 3, 2012

(54) FUEL PROPERTY DETECTION APPARATUS

(75) Inventors: Rie Osaki, Anjo (JP); Naoyo Kato, Ama-gun (JP); Noriyasu Amano, Gamagori (JP); Satoshi Taniguchi, Numazu (JP); Kaori Yoshida, Susono (JP); Yukihiro Tsukasaki, Susono (JP)

(73) Assignees: Nippon Soken, Inc., Aichi (JP); Toyota Jidosha Kabushiki Kaisha, Toyota (JP)

( * ) Notice: Subject to any disclaimer, the term of this patent is extended or adjusted under 35 U.S.C. 154(b) by 127 days.

(21) Appl. No.: 12/311,425

(22) PCT Filed: May 14, 2008

(86) PCT No.: PCT/JP2008/058827
§ 371 (c)(1),
(2), (4) Date: Mar. 30, 2009

(87) PCT Pub. No.: WO2008/143080
PCT Pub. Date: Nov. 27, 2008

(65) Prior Publication Data
US 2010/0020325 A1    Jan. 28, 2010

(30) Foreign Application Priority Data
May 15, 2007  (JP) .................................. 2007-129143

(51) Int. Cl.
*G01N 21/00* (2006.01)
(52) U.S. Cl. ................ 356/436; 356/432; 250/343
(58) Field of Classification Search .......... 356/432–440; 250/343, 339.13, 344, 341; 73/61–47, 61.44
See application file for complete search history.

(56) References Cited

U.S. PATENT DOCUMENTS
5,015,091 A * 5/1991 Suzuki et al. ................. 356/135
5,126,570 A * 6/1992 Boos ............................. 250/343
(Continued)

FOREIGN PATENT DOCUMENTS
JP           A-62-88942           4/1987
(Continued)

OTHER PUBLICATIONS

International Preliminary Report on Patentability issued in International Application No. PCT/JP2008/058827 on Nov. 24, 2009.
(Continued)

*Primary Examiner* — Sang Nguyen
(74) *Attorney, Agent, or Firm* — Oliff & Berridge, PLC

(57) ABSTRACT

It is an object of the present invention to provide a fuel property detection apparatus that excels in durability and reliability and is capable of accurately detecting the biofuel concentration in a mixture of hydrocarbon fuel and biofuel with a compact and simple configuration. A fuel property sensor 22 includes a light-emitting device 28 and a light-receiving device 32, which detect the optical transmittance of a fuel in a fuel path 26; and a light-emitting device 36 and a position sensitive device 38, which detect the refractive index of the fuel. As the optical transmittance correlates with the RME concentration of the fuel, the RME concentration can be calculated from the detected optical transmittance. As the refractive index correlates with the cetane number of the fuel, the cetane number can be calculated from the detected refractive index. The optical transmittance is detected through the use of light within a wavelength range of 640 nm to 680 nm.

14 Claims, 4 Drawing Sheets

U.S. PATENT DOCUMENTS

| | | | | |
|---|---|---|---|---|
| 5,157,452 | A | * | 10/1992 | Suzuki et al. .................. 356/128 |
| 5,239,860 | A | * | 8/1993 | Harris et al. .................. 73/61.48 |
| 5,262,645 | A | * | 11/1993 | Lambert et al. .......... 250/339.04 |
| 5,414,367 | A | * | 5/1995 | Ogawa ........................... 324/663 |
| 5,515,280 | A | * | 5/1996 | Suzuki ............................. 701/29 |
| 5,691,701 | A | * | 11/1997 | Wohlstein et al. ............ 340/603 |
| 5,739,916 | A | * | 4/1998 | Englehaupt ................... 356/414 |
| 5,793,043 | A | * | 8/1998 | Weckstrom et al. ..... 250/339.13 |
| 6,536,262 | B2 | * | 3/2003 | Baldauf et al. ............... 73/61.47 |

FOREIGN PATENT DOCUMENTS

| | | | |
|---|---|---|---|
| JP | A-1-244341 | | 9/1989 |
| JP | A-1-272941 | | 10/1989 |
| JP | A-4-55758 | | 2/1992 |
| JP | A-4-501769 | | 3/1992 |
| JP | A-05-133886 | | 5/1993 |
| JP | 05223733 | A * | 8/1993 |
| JP | A-05-223026 | | 8/1993 |
| JP | A-10-019775 | | 1/1998 |
| JP | A-2005-017018 | | 1/2005 |
| JP | A-2005-138062 | | 6/2005 |

OTHER PUBLICATIONS

International Search Report issued in International Application No. PCT/JP2008/058827 on Aug. 5, 2008 (with translation).

Sadeghi-Jorabchi et al., "Estimation of bio-diesel in lubricating oil using Fourier transform infrared spectroscopy combined with a mid-infrared fibre optic probe," *Spectroscopy Europe*, 1994, pp. 16-21.

Zawadzki et al., "Use of a spectrophotometer for biodiesel quality sensing," The Society for engineering in agricultural, food, and biological systems, An ASAE Meeting Presentation, Paper No. 053133, Jul. 17-20, 2005.

Jun. 21, 2011 Office Action issued in Japanese Patent Application No. 2007-129143.

* cited by examiner

FUEL PROPERTY DETECTION APPARATUS

TECHNICAL FIELD

The present invention relates to a fuel property detection apparatus.

BACKGROUND ART

In recent years, the use of biofuel, which is extracted, for instance, from sugarcane, corn, or wood, is promoted. As part of such promotional efforts, studies are being conducted on mixing a light oil with a biofuel (methyl ester) made, for instance, from rapeseed oil and using the resulting mixture as a diesel engine fuel.

When using the above-mentioned mixed fuel, it is necessary, for instance, to provide fuel injection control in accordance with biofuel concentration for the purpose of maintaining, for instance, adequate ignition performance. It is therefore important that the concentration of biofuel in the fuel supplied to a diesel engine be detected with high accuracy.

An apparatus disclosed in JP-A-1993-133886 uses the permittivity difference between alcohol and gasoline, measures the capacitance between a pair of electrode plates to detect alcohol concentration, and corrects the correlations between heaviness and refractive index in accordance with the detected alcohol concentration to determine the degree of heaviness.

Patent Document 1: JP-A-1993-133886
Patent Document 2: JP-A-1998-19775
Patent Document 3: JP-A-1993-223026

DISCLOSURE OF THE INVENTION

Problem to be Solved by the Invention

However, the above conventional apparatus does not detect the concentration, for instance, of rapeseed methyl ester. Further, the use of a method of detecting the biofuel concentration (alcohol concentration) on the basis of capacitance, which is used by the above conventional apparatus, entails the necessity of immersing the electrodes in fuel. Biofuels are likely to contain water. In the above conventional apparatus, therefore, the electrodes may be readily corroded by the water in the fuel. In addition, impurities in the fuel may adhere to the electrodes, thereby decreasing the accuracy of measurement or resulting in the inability to make measurements.

The present invention has been made in view of the above circumstances. An object of the present invention is to provide a fuel property detection apparatus that excels in durability and reliability and is capable of accurately detecting the biofuel concentration in a mixture of hydrocarbon fuel and biofuel with a compact and simple configuration.

Means for Solving the Problem

The above object is achieved by a first aspect of the present invention. The first aspect of the present invention is a fuel property detection apparatus that detects biofuel concentration in a mixture of hydrocarbon fuel and biofuel, comprising:
optical transmittance detection means for detecting optical transmittance of the fuel mixture with respect to light within a wavelength range of 640 nm to 680 nm; and
concentration calculation means for calculating the biofuel concentration in the fuel mixture on the basis of the optical transmittance detected by the optical transmittance detection means.

A second aspect of the present invention is the fuel property detection apparatus according to the first aspect, wherein the optical transmittance detection means includes a light-emitting device, which emits light for detecting the optical transmittance; and a corrective light-receiving device, which detects the amount of light emitted from the light-emitting device in order to correct the influence of a change in the amount of light emitted from the light-emitting device.

A third aspect of the present invention is the fuel property detection apparatus according to the first or the second aspect, further comprising:
refractive index detection means for detecting the refractive index of the fuel mixture; and
cetane number calculation means for calculating the cetane number of the fuel mixture on the basis of the refractive index detected by the refractive index detection means.

A fourth aspect of the present invention is the fuel property detection apparatus according to the third aspect, further comprising:
a light guide member;
wherein the light guide member is commonly used to guide optical transmittance detection light and refractive index detection light to the fuel mixture.

A fifth aspect of the present invention is the fuel property detection apparatus according to the fourth aspect, wherein the optical transmittance detection light and the refractive index detection light pass a common interface that is formed between the light guide member and the fuel mixture.

A sixth aspect of the present invention is the fuel property detection apparatus according to any one of the first to the fifth aspects, wherein the biofuel is mainly composed of methyl ester.

Advantages of the Invention

According to the first aspect of the present invention, the biofuel concentration in a mixture of hydrocarbon fuel and biofuel can be detected by determining the optical transmittance of the fuel mixture with respect to light having a wavelength between 640 nm and 680 nm and performing calculations on the determined optical transmittance. The optical transmittance varies with the biofuel concentration. However, the variation is obvious within a wavelength range of 640 nm to 680 nm. The first aspect of the present invention makes it possible to detect the biofuel concentration with high accuracy because it allows the use of the transmittance of light within the above-mentioned wavelength range.

According to the second aspect of the present invention, the influence of a change in the amount of light emitted from a light-emitting device can be corrected by allowing a corrective light-receiving device to detect the amount of light emitted from the light-emitting device. Therefore, the biofuel concentration can be detected with high accuracy irrespective of a change in the amount of light emitted from the light-emitting device.

According to the third aspect of the present invention, the refractive index of the fuel mixture can be detected. Further, the cetane number of the fuel mixture can be calculated from the detected refractive index. This makes it possible to determine fuel properties with increased accuracy and control an internal combustion engine in a more appropriate manner.

According to the fourth aspect of the present invention, a common light guide member can be used to guide optical transmittance detection light to the fuel mixture and guide refractive index detection light to the fuel mixture. Therefore, the number of required parts can be reduced to create a simple configuration. This makes it possible to achieve downsizing and manufacturing cost reduction.

According to the fifth aspect of the present invention, the optical transmittance detection light and the refractive index detection light pass a common interface formed between the light guide member and the fuel mixture. This makes it possible to downsize the light guide member and reduce the cost, for instance, of light guide member surface treatment.

According to the sixth aspect of the present invention, the concentration of methyl ester in the fuel mixture can be detected with high accuracy when the biofuel is mainly composed of methyl ester.

BEST MODE FOR CARRYING OUT THE INVENTION

First Embodiment

Description of System Configuration

Figure 1:
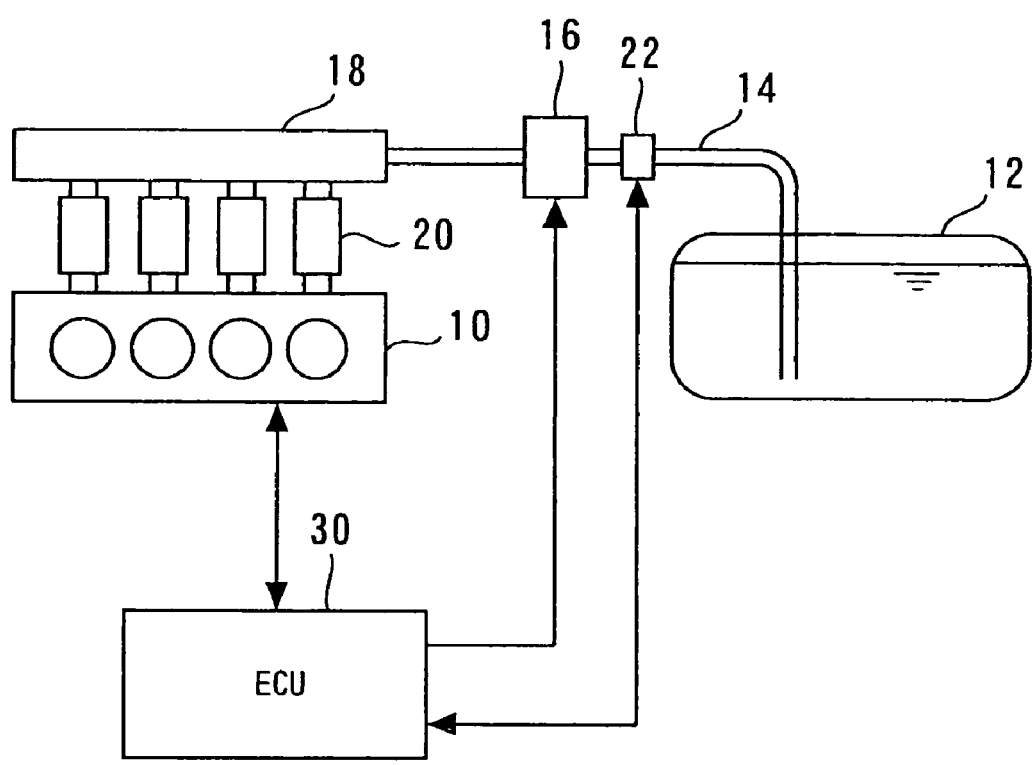
FIG. 1 is a diagram illustrating the configuration of a system according to a first embodiment of the present invention.

FIG. 1 is a diagram illustrating the configuration of a system according to a first embodiment of the present invention. As shown in FIG. 1, the system according to the first embodiment includes a diesel engine 10, which is mounted in a vehicle. The fuel for the diesel engine 10 is stored in a fuel tank 12. It is assumed that a fuel made of 100 percent light oil or a fuel mixture of light oil and rapeseed methyl ester is supplied to the fuel tank 12.

The fuel in the fuel tank 12 is transferred toward the diesel engine 10 through a fuel pipe 14. A supply pump 16 is installed in the middle of the fuel pipe 14. The fuel is pressurized by the supply pump 16. The resulting high-pressure fuel is stored in a common rail 18. The common rail 18 distributes the fuel to an injector 20 for each cylinder.

A fuel property sensor 22 is also installed in the middle of the fuel pipe 14. The fuel property sensor 22 can detect the optical transmittance and refractive index of the fuel passing through the fuel pipe 14.

The system also includes an ECU (Electronic Control Unit) 30. The ECU 30 is electrically connected not only to the injector 20 and fuel property sensor 22 but also to various sensors and actuators that control the diesel engine 10. On the basis of an output from the fuel property sensor 22, the ECU 30 is capable of determining the concentration of rapeseed methyl ester (hereinafter abbreviated to "RME") in the fuel supplied to the diesel engine 10 and the cetane number of the fuel, as described later.

Figure 2:
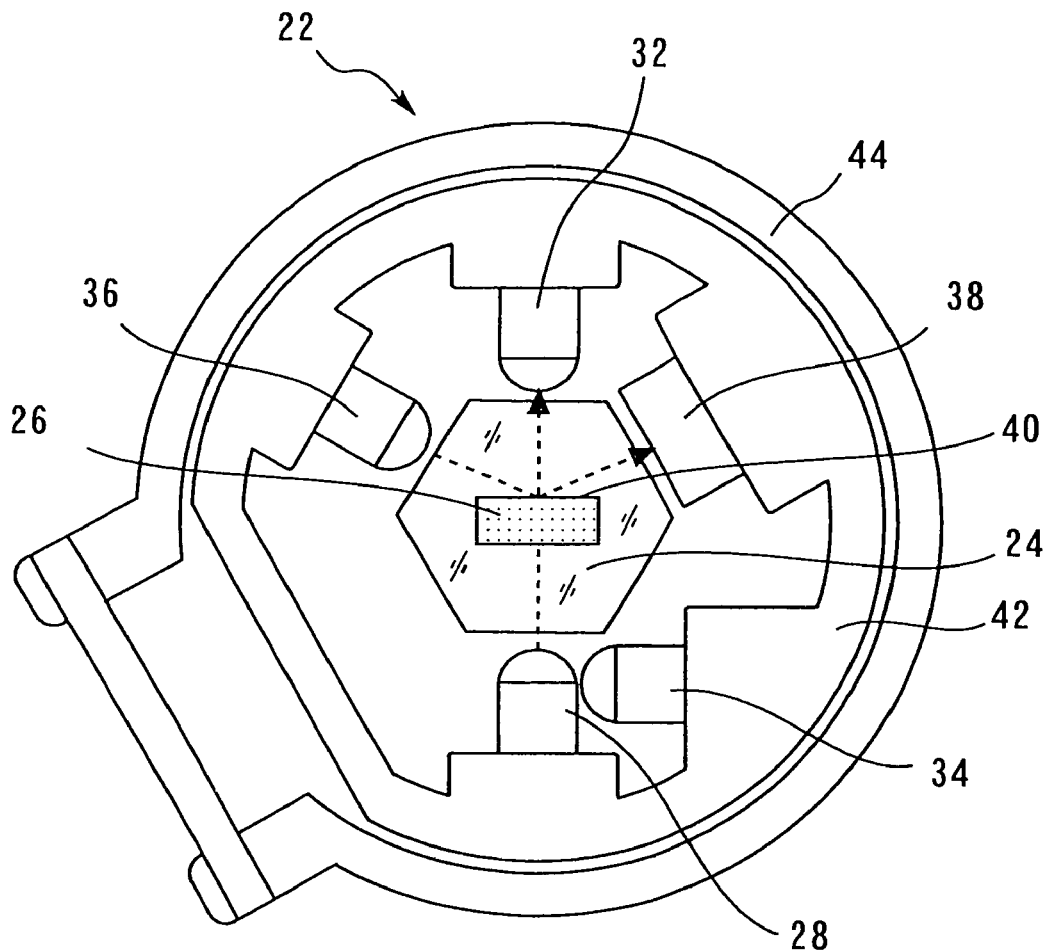
FIG. 2 is a diagram illustrating the internal structure of a fuel property sensor.

FIG. 2 is a diagram illustrating the internal structure of the fuel property sensor 22. The fuel property sensor 22 will now be described in detail with reference to FIG. 2. It should be noted that FIG. 2 is a view taken in a direction parallel to the fuel pipe 14. It means that the fuel pipe 14 is extended in a direction perpendicular to the paper surface of FIG. 2.

The fuel property sensor 22 includes a prism 24, which is shaped like a hexagonal column. A fuel path 26, which is a rectangular through-hole, is formed in the prism 24. The fuel path 26 is filled with the fuel supplied from the fuel pipe 14.

A light-emitting device 28 is installed near one side of the prism 24 to emit light for detecting the optical transmittance of the fuel. A light-receiving device 32 is installed near the opposite side of the prism 24, which is parallel to the above-mentioned side. The light emitted from the light-emitting device 28 is incident on the prism 24, transmitted through the fuel in the fuel path 26, and received by the light-receiving device 32. The light-receiving device 32 generates an output according to the amount of received light by converting the received light to electricity. The higher the optical transmittance of the fuel in the fuel path 26 is, the larger the amount of light incident on the light-receiving device 32 is, and thus the greater the output of the light-receiving device 32 becomes. Consequently, the optical transmittance (or absorbance) of the fuel can be detected in accordance with the output of the light-receiving device 32.

Further, a corrective light-receiving device 34 is installed near the light-emitting device 28 to detect the amount of light emitted from the light-emitting device 28. In general, the amount of light emitted from the light-emitting device 28 changes (decreases) when the ambient temperature rises. Therefore, the output of the light-receiving device 32 varies with the temperature even when the optical transmittance of the fuel remains unchanged. Consequently, correction is made on the basis of a light emission amount detected by the corrective light-receiving device 34 for the purpose of neutralizing the effect of temperature-induced changes in the amount of light emitted from the light-emitting device 28.

Another light-emitting device 36 is installed near another side of the prism 24 to emit light for detecting the refractive index of the fuel. A position sensitive device (PSD) 38 is installed near another side of the prism 24, which is inclined toward the above-mentioned side.

Figure 3:
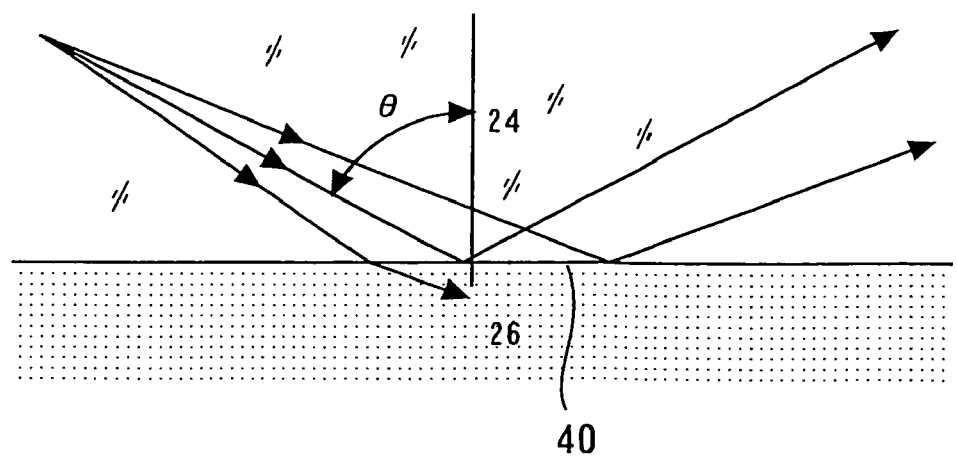
FIG. 3 is a diagram illustrating how light behaves when it reaches an interface.

The light emitted from the light-emitting device 36 enters the prism 24 and obliquely reaches an interface 40 between the fuel and the inner wall of the fuel path 26. FIG. 3 is a diagram illustrating how the light behaves when it reaches the interface 40. As shown in FIG. 3, the light reaching the interface 40 totally reflects from the interface 40 when its incidence angle to the normal line of the interface 40 is larger than a critical angle $\theta$ or becomes refracted at the interface 40 and enters the fuel when its incidence angle to the normal line of the interface 40 is smaller than the critical angle $\theta$. When the refractive index of the prism 24 is $N_1$ and the refractive index of the fuel is $N_2$, the critical angle $\theta$ is expressed by the following equation:

$$N_2 = N_1 \times \sin\theta \quad (1)$$

As shown in FIG. 2, the light reflected from the interface 40 travels through the prism 24 and becomes incident on the light-receiving surface of the position sensitive device 38. The position sensitive device 38 generates an output that expresses the gravity center position of the incident light on the light-receiving surface.

Equation (1) above indicates that the higher the refractive index $N_2$ of the fuel, the larger the critical angle $\theta$. As described above, the light emitted from the light-emitting device 36 does not reflect from the interface 40 when its incidence angle to the normal line of the interface 40 is smaller than the critical angle $\theta$ and therefore does not reach the position sensitive device 38. Further, the larger the critical angle θ, the larger the incidence angle range within which the light does not reflect from the interface 40. Therefore, increasing the critical angle θ decreases the light incidence area of the light-receiving surface of the position sensitive device 38. This changes the gravity center position of the light detected by the position sensitive device 38. It means that there is a correlation between the refractive index of the fuel and the gravity center position of the light detected by the position sensitive device 38. Thus, the refractive index of the light can be detected from the output of the position sensitive device 38.

For example, an LED (Light-Emitting Diode) may be used as the light-emitting devices 28, 39. Further, a photodiode (PD) may be used as the light-receiving device 32 and corrective light-receiving device 34. The light-emitting devices and light-receiving devices 28, 32, 34, 36 and position sensitive device 38 are positioned and retained by a holder 42. The holder 42 is placed in a housing 44.

(RME Concentration Detection Method)

The RME concentration of a fuel mixed with RME correlates with optical transmittance. Therefore, the ECU 30 can calculate the RME concentration of the fuel supplied to the diesel engine 10 on the basis of the optical transmittance detected by the fuel property sensor 22.

Figure 4:
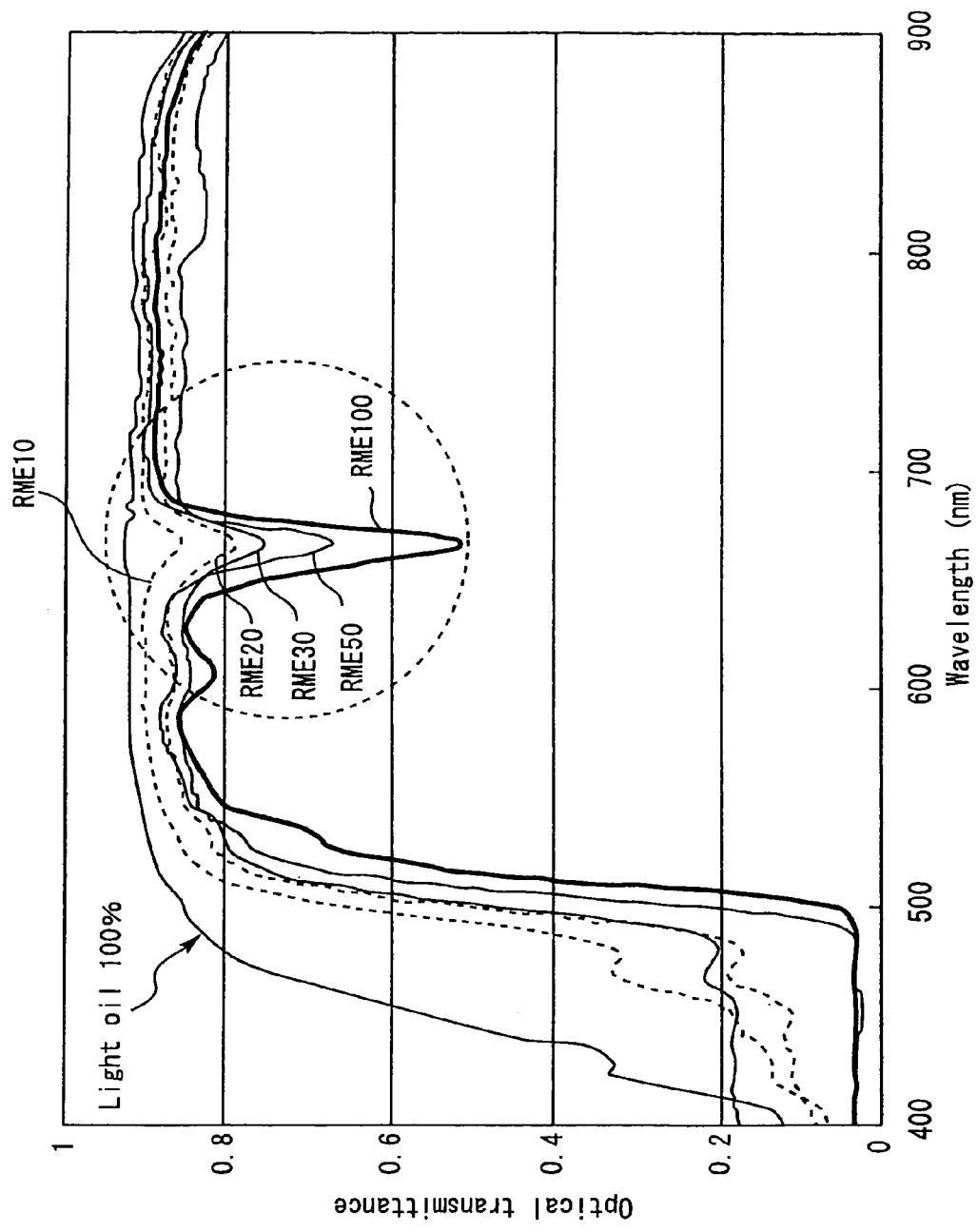
FIG. 4 is a diagram illustrating a wavelength characteristic of optical transmittance of fuels that differ in RME concentration.

FIG. 4 is a diagram illustrating the wavelength characteristic of the optical transmittance of fuels that differ in RME concentration. More specifically, FIG. 4 shows graphs illustrating the wavelength characteristics of a fuel made of 100 percent light oil, a fuel mixture containing 10 percent RME (RME10), a fuel mixture containing 20 percent RME (RME 20), a fuel mixture containing 30 percent RME (RME 30), a fuel mixture containing 50 percent RME (RME50), and a fuel made of 100 percent RME (RME100).

As shown in FIG. 4, the higher the RME concentration, the lower the optical transmittance. The optical transmittance difference based on the difference in RME concentration is obvious particularly within a wavelength range of 640 nm to 680 nm. Therefore, the present invention uses light (red light) within a wavelength range of 640 nm to 680 nm to detect the optical transmittance of fuel. This makes it possible to detect the RME concentration of fuel with high accuracy.

Optical transmittance detection through selective use of light within the above wavelength range can be achieved by using a device having an emission wavelength within the above wavelength range as the light-emitting device 28. An alternative would be to employ a device having a wide emission wavelength range and use an optical filter to select light within the above wavelength range.

Figure 5:
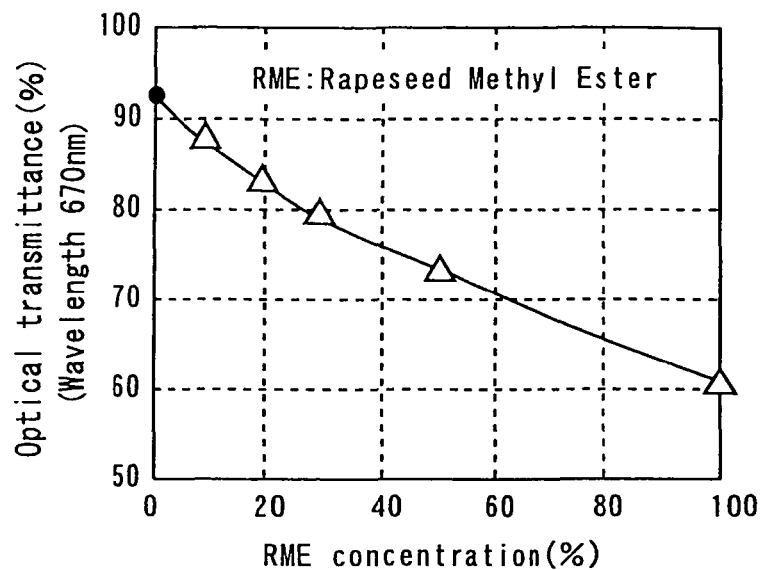
FIG. 5 is a map defining the relationship between optical transmittance and RME concentration that prevails during the use of light having a wavelength of 670 nm.

FIG. 5 is a map defining the relationship between optical transmittance and RME concentration that prevails during the use of light having a wavelength of 670 nm. The present embodiment assumes that a map similar to the one shown in FIG. 5 is stored beforehand in the ECU 30 in accordance with the wavelength to be used. The map can be used to calculate the RME concentration of fuel in accordance with the optical transmittance detected by the fuel property sensor 22.

(Cetane Number Detection Method)

The cetane number or cetane index (generically referred to as the cetane number in this document) of fuel correlates with refractive index. Therefore, the ECU 30 can calculate the cetane number of the fuel supplied to the diesel engine 10 on the basis of the refractive index detected by the fuel property sensor 22.

Figure 6:
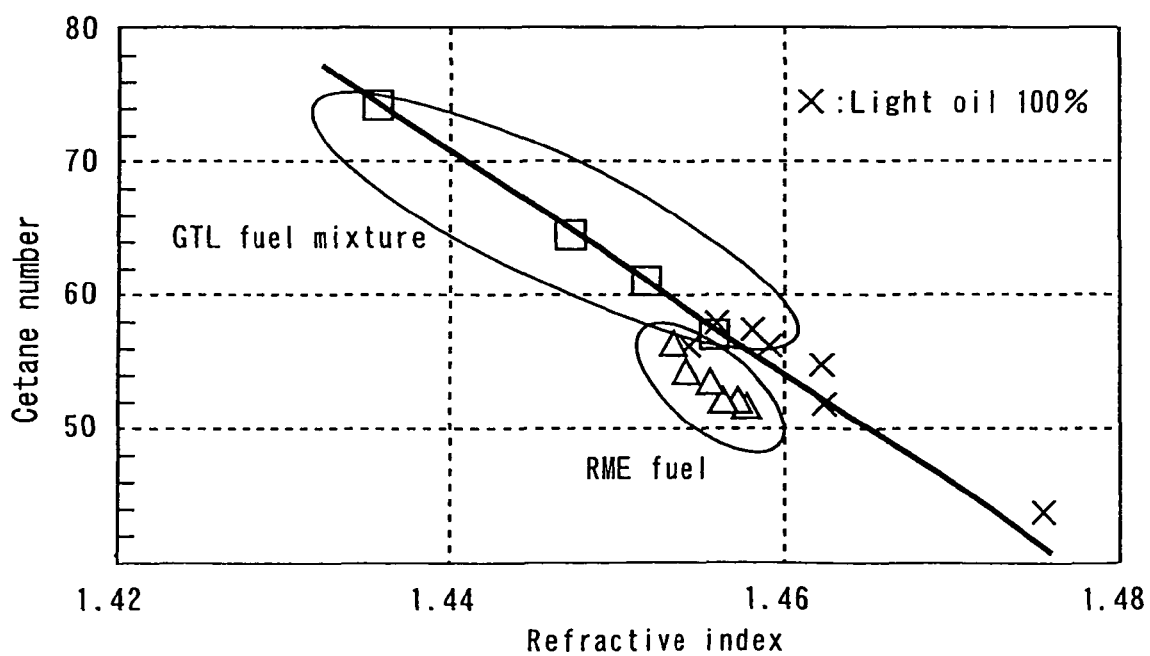
FIG. 6 is a diagram illustrating the relationship between cetane number and refractive index.

FIG. 6 is a diagram illustrating the relationship between cetane number and refractive index. In FIG. 6, the x mark represents a case where a fuel made of 100 percent light oil is used; the triangular mark represents a case where a fuel mixture containing RME is used; and the rectangular mark represents a case where a GTL (Gas To Liquid) fuel mixture is used (reference information).

As shown in FIG. 6, the relationship represented by a straight line in FIG. 6, that is, the relationship in which the cetane number increases with a decrease in the refractive index, is established no matter which fuel is used. The present embodiment assumes that the relationship indicated by the straight line in FIG. 6 is expressed as a map and stored beforehand in the ECU 30. The map can be used to calculate the cetane number of a fuel in accordance with the refractive index detected by the fuel property sensor 22.

Light outside a wavelength range of 640 nm to 680 nm is preferably used as the light for detecting the refractive index, that is, the light to be emitted from the light-emitting device 36. The use of such light, which is insignificantly absorbed by an RME fuel mixture, makes it possible to detect the refractive index with increased accuracy.

As described above, the present embodiment can accurately detect the RME concentration and cetane number of a fuel. Thus, control can be exercised, for instance, over the amount of fuel injection from the injector 20, the timing of fuel injection, the use of a pilot injection function, and the number of pilot injections on the basis of the detected RME concentration and cetane number. This makes it possible to obtain, for instance, sufficient ignition performance and operate the diesel engine 10 properly, regardless of the REM concentration and cetane number of a fuel supplied to the diesel engine 10.

Further, the fuel property sensor 22 is configured to optically detect both an index (optical transmittance) for determining the RME concentration of a fuel and an index (refractive index) for determining the cetane number of the fuel, as described above. The use of such a configuration provides three advantages described below. The first advantage is that an electrode and other parts of the fuel property sensor 22 do not need to be in contact with fuel. When the electrode or other metal part is in contact with a biofuel, which readily contains water, a problem such as corrosion is likely to occur. However, the use of the fuel property sensor 22 makes it possible to avoid such a problem, thereby providing excellent durability. The second advantage is that an optical detection scheme is employed to substantially avoid the influence of impurities in the fuel. This makes it possible to achieve high-accuracy detection at all times, thereby providing high reliability. The third advantage is that the fuel property sensor 22 can be readily downsized to reduce its size. This increases the degree of freedom in installation location selection for the fuel property sensor 22.

Furthermore, the fuel property sensor 22 according to the present embodiment uses the common prism 24 in such a manner that the light for optical transmittance detection, that is, the light emitted from the light-emitting device 28, and the light for refractive index detection, that is, the light emitted from the light-emitting device 36, are guided to the fuel. Therefore, the number of required parts can be reduced to create a simple configuration. This makes it possible to achieve downsizing and manufacturing cost reduction.

Moreover, the present embodiment is configured so that the light for optical transmittance detection and the light for refractive index detection pass through the common interface 40. This makes it possible to downsize the prism 24 and reduce the cost, for instance, of surface treatment of the prism 24.

The present embodiment has been described on the assumption that rapeseed methyl ester, which is made from rapeseed oil, is used as the biofuel. However, the present invention is not limited to the use of rapeseed-derived methyl ester. Methyl ester made from any biomass may be used as the biofuel. Further, not only methyl ester but also the other types of fuel may be used as the biofuel. Furthermore, not only light oil but also the other types of fuel may be used as the hydrocarbon fuel (fossil fuel) to be mixed with the biofuel.

The invention claimed is:

1. A fuel property detection apparatus that detects biofuel concentration in a mixture of hydrocarbon fuel and biofuel, comprising:

optical transmittance detection means for detecting optical transmittance of the fuel mixture with respect to light within a wavelength range of 640 nm to 680 nm; and concentration calculation means for calculating the biofuel concentration in the fuel mixture on the basis of the optical transmittance detected by the optical transmittance detection means, wherein the optical transmittance detection means includes a light-emitting device, which emits light for detecting the optical transmittance; and a corrective light-receiving device, which detects the amount of light emitted from the light-emitting device in order to correct the influence of a change in the amount of light emitted from the light-emitting device.

2. The fuel property detection apparatus according to claim 1, further comprising:

refractive index detection means for detecting the refractive index of the fuel mixture; and cetane number calculation means for calculating the cetane number of the fuel mixture on the basis of the refractive index detected by the refractive index detection means.

3. The fuel property detection apparatus according to claim 2, further comprising:

a light guide member;

wherein the light guide member is commonly used to guide optical transmittance detection light and refractive index detection light to the fuel mixture.

4. The fuel property detection apparatus according to claim 3, wherein the optical transmittance detection light and the refractive index detection light pass a common interface that is formed between the light guide member and the fuel mixture.

5. The fuel property detection apparatus according to claim 1, wherein the biofuel is mainly composed of methyl ester.

6. The fuel property detection apparatus according to claim 1, wherein the corrective light-receiving device is on a same side of the fuel mixture as the light-emitting device.

7. The fuel property detection apparatus according to claim 1, the optical transmittance detection means further including a light-receiving device that receives light transmitted from the light-emitting device through the fuel mixture.

8. A fuel property detection apparatus that detects biofuel concentration in a mixture of hydrocarbon fuel and biofuel, comprising:

an optical transmittance detection device for detecting optical transmittance of the fuel mixture with respect to light within a wavelength range of 640 nm to 680 nm; and a concentration calculation device for calculating the biofuel concentration in the fuel mixture on the basis of the optical transmittance detected by the optical transmittance detection device, wherein the optical transmittance detection device includes a light-emitting device, which emits light for detecting the optical transmittance; and a corrective light-receiving device, which detects the amount of light emitted from the light-emitting device in order to correct the influence of a change in the amount of light emitted from the light-emitting device.

9. The fuel property detection apparatus according to claim 8, further comprising:

a refractive index detection device for detecting the refractive index of the fuel mixture; and a cetane number calculation device for calculating the cetane number of the fuel mixture on the basis of the refractive index detected by the refractive index detection device.

10. The fuel property detection apparatus according to claim 9, further comprising:

a light guide member;

wherein the light guide member is commonly used to guide optical transmittance detection light and refractive index detection light to the fuel mixture.

11. The fuel property detection apparatus according to claim 10, wherein the optical transmittance detection light and the refractive index detection light pass a common interface that is formed between the light guide member and the fuel mixture.

12. The fuel property detection apparatus according to claim 8, wherein the biofuel is mainly composed of methyl ester.

13. The fuel property detection apparatus according to claim 8, wherein the optical transmittance detection device includes a light-emitting device, which emits light for detecting the optical transmittance, the fuel property detection apparatus further comprising:

a corrective light-receiving device, which detects the amount of light emitted from the light-emitting device in order to correct the influence of a change in the amount of light emitted from the light-emitting device, the corrective light-receiving device being on a same side of the fuel mixture as the light-emitting device.

14. The fuel property detection apparatus according to claim 8, the optical transmittance detection device further including a light-receiving device that receives light transmitted from the light-emitting device through the fuel mixture.

* * * * *

UNITED STATES PATENT AND TRADEMARK OFFICE
CERTIFICATE OF CORRECTION

| | | |
|---|---|---|
| PATENT NO. | : 8,089,629 B2 | Page 1 of 1 |
| APPLICATION NO. | : 12/311425 | |
| DATED | : January 3, 2012 | |
| INVENTOR(S) | : Rie Osaki et al. | |

It is certified that error appears in the above-identified patent and that said Letters Patent is hereby corrected as shown below:

Title page, Item (75), inventor change "Naoyo Kato" to --Naoya Kato--.

Signed and Sealed this
Twenty-fourth Day of April, 2012

David J. Kappos
*Director of the United States Patent and Trademark Office*